United States Patent [19]

Bialy et al.

[11] Patent Number: 4,568,662

[45] Date of Patent: Feb. 4, 1986

[54] PROCESS FOR PREPARING ALKYLATION CATALYSTS

[75] Inventors: Jan Bialy; Irena Penczek; Nikuca Kopytowska, all of Warsaw; Jòsef Wrzyszcz, Wroclaw; Jolanta Cmièlowska, Wroclaw; Hanna Grabowska, Wroclaw; Wlodzimierz Kaczmarczyk, Wroclaw; Kazimierz Mazur, Wroclaw; Wlodzimierz Mista, Wroclaw, all of Poland

[73] Assignee: Enichimica S.p.A., Milan, Italy

[21] Appl. No.: 677,230

[22] Filed: Dec. 3, 1984

[30] Foreign Application Priority Data

Dec. 5, 1983 [IT] Italy .............................. 24021 A/83

[51] Int. Cl.$^4$ ..................... B01J 23/26; B01J 23/74; B01J 23/86
[52] U.S. Cl. .................................... 502/257; 502/256; 502/258; 502/305; 502/310; 502/311; 502/316; 502/317; 502/330; 502/338; 568/794; 568/804
[58] Field of Search ............... 502/256, 257, 258, 305, 502/310, 311, 316, 317, 330, 338; 568/794, 804

[56] References Cited

U.S. PATENT DOCUMENTS 4,227,024 10/1980 Leach .................................. 568/804
4,329,517 5/1982 Taniguchi et al. ............. 502/338 X Primary Examiner—W. J. Shine
Attorney, Agent, or Firm—Hedman, Gibson, Costigan & Hoare

[57] ABSTRACT

Preparation of alkylation catalysts containing iron oxide and/or chromium oxide, by means of a process which comprises:

(a) precipitating hydrate oxides of iron and/or chromium from an aqueous solution of soluble compounds of said elements;
(b) separating the thus obtained precipitate, and washing said precipitate;
(c) granulating the washed precipitate, and drying the granules so obtained;
(d) calcining said dried granules at high temperature;

in which an organic carboxylic acid salt of iron and/or chromium is added to and homogenized with the washed precipitate from stage (b), and/or the dried granules from stage (c) are impregnated with an aqueous solution of an organic carboxylic acid salt of iron and/or chromium.

The catalysts obtained by means of the above process are mechanically strong, and highly active in the production process of 2,6-xylenol by means of the alkylation of phenol or o-cresol with methanol.

11 Claims, No Drawings

PROCESS FOR PREPARING ALKYLATION CATALYSTS

The present invention relates to an improved process for preparing catalysts on the basis of iron and/or chromium, active in the alkylating process of phenol or o-cresol with methanol, to 2,6-xylenol.

2,6-Xylenol is useful as raw material for the preparation of polyphenyleneoxide, a valuable thermoplastic polymer, used in the art mainly admixed to polymers and copolymers of styrene.

2,6-Xylenol can be obtained by means of the alkylation of phenol or o-cresol with methanol, on catalysts generally consisting of mixtures of metal oxides. Among catalysts known, are the mixtures of iron, silicon, chromium, antimony and vanadium oxides, as disclosed in the Polish Pat. No. 105,922, or the mixtures of oxides of iron, chromium, silicon and potassium, as disclosed in the German Pat. No. 2,547,309, or the mixtures of oxides of iron, tin, chromium and phosphorus, as described in the U.S. Pat. No. 4,227,024. Other catalysts known contain oxides of chromium, tin and copper (Jap. Appl. No. 81/55327), or oxides of vanadium, tin and silicon (Jap. Pat. Appl. No. 81/133232), or oxides of vanadium and chromium and/or manganese (Jap. Pat. Appl. No. 81/135434).

The process for preparing such catalysts comprises generally the precipitation or co-precipitation of hydrate oxides of the metals from the aqueous solutions of respective soluble compounds, by means of the addition of alkalies such as ammonia, alkaline hydroxides and acid carbonates, the granulation of the so obtained precipitate, the drying and calcination of said granules.

The catalysts prepared by means of the known processes generally show the disadvantage due to a too short life under the alkylation conditions of phenol or o-cresol, because of a loss in activity presumably due to an incorrect structure and pore distribution. To the purpose of obviating such a drawback, compounds of phosphorus have been introduced inside the catalysts, capable of developing a good microporous structure.

Such an expedient however, if on one side it allows the structure of the catalyst to be improved, on the other side causes a drop of its mechanical characteristics, which is mainly evidenced by the lower resistance to grinding under operating conditions.

The purpose of the present invention is therefore the overcoming of the drawbacks mentioned above, by means of a process for the production of catalysts on the basis of oxides of iron and/or chromium, which are characterized, in addition to the mechanical strength, by high values of activity and selectivity in the process of production of 2,6-xylenol by the alkylation of phenol or o-cresol with methanol.

The present invention is essentially based on the fact of supplying iron and/or chromium, in the preparation process of the catalyst, partly as a salt of organic acid, in particular stages of the process itself, that which allows the catalyst to be improved, likely in that its structure is developed by increasing its content in macropores, in comparison to the catalysts obtained by means of the process presently known in the art.

Accordingly, in the present invention, alkylation catalysts are prepared, containing oxides of iron and/or chromium, by means of a process which comprises:

(a) to precipitate the hydrate oxides of iron and/or chromium from aqueous solutions of soluble compounds of said elements;

(b) to separate the so obtained precipitate and to wash said separated precipitate;

(c) to granulate the washed precipitate and to dry the so obtained granules;

(d) to calcine said dried granules at high temperature; the process being characterized in that an organic carboxylic acid salt of iron and/or chromium is added to and homogenized with the washed precipitate from stage (b), and/or the dried granules from stage (c) are impregnated with an aqueous solution of organic carboxylic acid salt of iron and/or chromium; the quantity of such organic carboxylic acid salts being such as to supply a quantity of iron and/or chromium comprised within the range of from 5 to 60% referring to the content of such elements within the catalyst finally obtained.

According to the process of this invention, the hydrate oxides of iron and/or chromium are first precipitated (stage a)) from aqueous solutions of soluble compounds of said elements. Compounds suitable to this purpose are ferric nitrate, chromic nitrate and chromic acid. Within the aqueous solution, compounds of other elements may be present, e.g. of antimony and tin, generally as halides, mainly chlorides. Desirably, also an alkaline silicate is present inside the solution, mainly sodium silicate. The precipitation takes place by adding an alkali, mainly aqueous ammonia, to the aqueous solution of the above specified compounds, up to a pH value of about 7, or anyway up to pH values at which the hydrate oxides of the above specified elements are precipitated. Precipitation can be effected at temperature values of from room temperature (20°–25° C.) up to about 70° C.

The so obtained precipitate is separated, and submitted to washing (stage (b)). In particular, should the nitrate salts be used in the preceding stage (a), washing by deionized water is carried out until nitrate ions disappear from washing waters.

According to an embodiment of this invention, the washed precipitate thus obtained is mixed with an organic carboxylic acid salt of iron and/or chromium. To this purpose, the salts are particularly useful of mono- and dicarboxylic acid salts, containing up to 8 carbon atoms in the molecule. Examples thereof are the ferric and chromic salts of oxalic, benzoic, formic, acetic and citric acid. After the mixing, the mixture is granulated, and the granules are dried at temperatures of from about 95° to about 120° C.

According to another embodiment, the washed and dried precipitate from stage (b) is granulated, and the granules so obtained are dried at temperatures of from about 95° to about 120° C. (stage (c)), and then impregnated with an aqueous solution of iron and/or chromium salts of the organic carboxylic acids above listed. After the impregnation, the impregnated granules are dried, always operating at temperatures within the range of from about 95° to about 120° C.

According to a further embodiment, the iron and/or chromium salts of organic carboxylic acids are partly supplied by mixing them with the washed precipitate from stage (b), and partly are supplied by impregnating the dried granules from stage (c). It is important anyway that from 5 to 60% of iron and/or chromium, relatively to the final content within the ready-for-use catalyst, be supplied as an organic carboxylic acid salt.

According to a variant of the above mentioned embodiments, the dried granules from stage (c) are treated with an aqueous solution of sulphuric acid, and then dried, before being impregnated with the aqueous solution of the iron and/or chromium salt of organic carboxylic acids.

According to another variant of the above mentioned embodiments, the washed precipitate from stage (b) is mixed with a vanadate salt, mainly ammonium metavanadate, before being homogenized with the iron and/or chromium salt of organic carboxylic acids.

According to a further variant of the above mentioned embodiments, the granules are impregnated, immediately before being submitted to the calcination treatment, with a salt, mainly a carbonate, of alkali metal, mainly potassium, and the so impregnated granules are dried by heating them up to 180° C.

The calcination (stage (d)) is suitably effected at 300°–500° C. for 3–10 hours, operating in an oxidizing atmosphere, or in a reducing atmosphere, or in an inert atmosphere, e.g., under nitrogen. The catalysts according to this invention therefore comprise iron and/or chromium as fundamental elements, and may contain lower quantities of other elements, such as silicon, antimony, tin, vanadium and potassium.

In any case, the catalysts produced by means of the previously disclosed process, show a well developed pore structure, with a macropore content greater than that obtainable by means of the process according to the present art.

The catalysts of the present invention show an increased stability, and a longer operating life under the alkylating conditions, said operating life can indeed exceed 1,500 hours, before the regeneration of the catalyst be required.

The alkylating of phenol or of o-cresol with methanol, in particular, is carried out by feeding such reactants, together with water, to the catalyst as a fixed bed in a suitable reaction vessel, operating at temperatures of 320°–360° C.

Generally molecular ratios are used of phenol (o-cresol):methanol:water of about 1:5:1, and the reaction mixture is fed at a rate of about 0.5 volumes, per volume of reactor, per hour.

The following experimental Examples are illustrative and not limitative of the invention. Example 1 is shown to comparison purposes with the presently known art.

EXAMPLE 1 (COMPARISON)

An aqueous solution is prepared, containing 500 g of ferric nitrate, 4.95 g of chromic nitrate and 2.75 g of sodium silicate. The formation is caused of a precipitate by adding an aqueous solution containing 10% by weight of ammonia, up to a pH value of 7, operating at room temperature. The precipitate is separated, washed with distilled water until nitrate ions disappear from washing waters. The washed precipitate is then dried at 180° C. for 10 hours, and granulated.

To 50 g of this granular solid, 7.5 ml are added of a solution obtained by mixing 1 g of potassium carbonate per 100 ml of solution, and the impregnated solid so obtained is dried at 180° C. and then calcined at 470° C. for 7 hours.

The alkylation catalyst so obtained shows the following characteristics:
Water absorption capacity: 0.14 ml/g;
crushing strength: 18 T/cm$^2$;
propensity to be ground: 4.2% (after two hours).

This catalyst has been produced by means of a well known process in the art, to the purpose of comparing its characteristics with those of the catalysts obtained according to the process of the present invention.

EXAMPLE 2

An aqueous solution is prepared containing 479.4 g of ferric nitrate and 2.75 g of sodium silicate. The formation of a precipitate is caused, by adding aqueous ammonia, at a concentration of 10% by weight, to the solution, up to a pH value of 7, operating at room temperature. The precipitate is separated and washed with distilled water, until nitrate ions disappear from washing waters. The washed precipitate is mixed with 9.16 g of iron oxalate. The mass so obtained is transformed into granules, and the granules are dried at 100° C.

The dried granules are then impregnated with an aqueous solution of chromium oxalate containing 0.64 g of chromium, as metal. The impregnated granules are then dried at 105° C. Potassium is then introduced, as potassium carbonate, as described in Example 1, and impregnated granules are dried at 180° C., and then calcined at 470° C. for 7 hours.

The so obtained catalyst has a water absorption capacity of 0.28 ml/g, and a specific surface area of 66 m$^2$/g.

EXAMPLE 3

An aqueous solution is prepared containing 223.3 g of ferric nitrate, 2.46 g of chromic nitrate and 2.75 g of sodium silicate. The formation of a precipitate is caused, by adding aqueous ammonia at a concentration of 10% by weight to the solution, up to a pH value of 7, operating at room temperature. The precipitate is separated and washed with distilled water, until nitrate ions disappear from washing waters. The washed precipitate is admixed with 240.1 g of ferric benzoate, the mixture is dried and granulated. The granules so obtained are impregnated with an aqueous solution of chromium acetate, containing 0.3 g of chromium, as metal, and impregnated granules are dried at 105° C. The process is then effected as in Example 1, by adding the potassium, as potassium carbonate, drying at 180° C., and calcining at 400° C.

The catalyst so obtained has a water absorption capacity of 0.31 mg/l.

EXAMPLE 4

An aqueous solution is prepared, containing 221 g of ferric nitrate, 4.95 of chromic nitrate and 2.75 g of sodium silicate. The formation of a precipitate is caused by adding aqueous ammonia, at a concentration of 10% by weight, to the solution, up to a pH value of 7, operating at room temperature. The precipitate is washed with distilled water until nitrate ions disappear from washing waters. Washed precipitate is admixed with 131.9 g of basic ferric acetate and the mixture so obtained is dried at 95° C. and granulated. Dried granules are calcined at 500° C., for 5 hours, in a reducing atmosphere.

The catalyst so obtained shows a water absorption capacity of 0.30 ml/g.

EXAMPLE 5

An aqueous solution is prepared containing 347.8 g of ferric nitrate, 4.95 g of chromic nitrate and 2.75 g of sodium silicate. The formation of a precipitate is caused by adding aqueous ammonia, at a concentration of 10% by weight, to the solution, up to a pH value of 7, operating at room temperature. The precipitate is washed with distilled water until nitrate ions disappear from washing waters. Washed precipitate is then admixed with 125.5 g of ferric citrate. The granulate obtained from this mass are dried at 100° C. Said dried granules (50 g) are impregnated with 7 ml of a solution containing 1,5 g of potassium carbonate per 100 ml of solution. Impregnated granules are dried at 100° C. and calcined at 450° C., for 10 hours, in an oxidizer atmosphere.

The so obtained catalyst shows a water absorption capacity of 0.34 ml/g.

EXAMPLE 6

An aqueous solution is prepared containing 383.6 g of ferric nitrate, 1.2 g of chromic nitrate, 0.23 g of antimony trichloride in tartaric acid and 0.8 g of sodium silicate. The formation of a precipitate is caused by adding aqueous ammonia at a concentration of 10% by weight to the solution, operating at 40° C. The precipitate is washed with distilled water, dried for 2 hours at 120° C. and then granulated. The granules are impregnated with an aqueous solution of ammonium metavanadate, containing 0.12 g of $NH_4VO_3$ and impregnated granules are dried at 110° C. Dried granules are then impregnated with an aqueous solution of iron formate, containing 2.81 g of iron as metal, dried and calcined at 450° C. for 10 hours.

The catalyst so obtained shows a water absorption capacity of 0.29 ml/g.

EXAMPLE 7

An aqueous solution is prepared containing 92.6 g of chromic nitrate, 10 ml of tin chloride $SnCl_2.H_2O$, and 10 g of ferric nitrate. The formation of a precipitate is caused by adding aqueous ammonia at 10% by weight to the solution, operating at 65° C. The precipitate is separated, washed with distilled water, dried at 105° C. for 3 hours, and granulated. Catalyst granules are impregnated with 100 ml of aqueous solution of 0.1N sulphuric acid, and impregnated granules are dried at 100° C. for 7 hours. The granules are then impregnated with an aqueous solution of chromic acetate containing 0.96 g of chromium, as metal, dried and calcined at 470° C. for 5 hours.

The catalyst so obtained shows a water absorption capacity of 0.27 ml/g.

EXAMPLE 8

An aqueous solution is prepared containing 18.6 g of chromic acid, 10 g of stannous chloride hydrate and 10 g of ferric nitrate. The formation of a precipitate is caused by adding aqueous ammonia at 10% by weight to the solution, operating at 70° C.

The precipitate is separated, washed with water and admixed with 48.5 g of chromic oxalate. The mixture is dried at 120° C. for 4 hours and granulated. The granules are impregnated with 100 ml of 0.1N aqueous sulphuric acid, dried at 115° C. for three hours and calcined in an inert atmosphere at 490° C. for 5 hours.

The catalyst so obtained shows the following characteristics:
Water absorption capacity: 0.29 ml/g;
crushing strength: 30 T/cm$^2$;
propensity to be ground: 0.9% (after 1 hour).

The catalysts prepared as in Examples 1 to 4 and 6 to 8 are used in the alkylating process of phenol with methanol, to yield 2,6-xylenol.

The tests, 100 hours long, are carried out in a reaction vessel operated at 338° C. by feeding 0.5 volumes, per each volume of catalyst and per hour, of a reaction mixture consisting of phenol, methanol and water in molar ratios to each other of 1:5:1.

The following results are obtained:

| Catalyst of Example No | Yield of 2,6-xylenol (% by volume) |
| --- | --- |
| 1 | 94.2 |
| 2 | 95.9 |
| 3 | 97.8 |
| 4 | 97.2 |
| 6 | 96.3 |
| 7 | 95.7 |
| 8 | 95.8 |

The catalysts of Examples 1 and 3 are additionally used, in the preceding process, operating at 340° C. for 420 hours. By the catalyst of Example 1, 2,6-xylenol is obtained in an average yield of 89.6%, and by the catalyst of Example 3, 2,6-xylenol is obtained in a yield of 97.5% in the average.

The catalysts of Examples 1, 5 and 8 are used in the methylation reaction of cresol to 2,6-xylenol, operating at 342° C. and feeding a reaction mixture consisting of o-cresol, methanol and water, in a molar ratio to each other of 1:5:1, at a rate of 0.5 volumes, per each volume of catalyst, and per hour. The tests, 50 hours long, give the following results:

| Catalyst of Example No | Yield of 2,6-xylenol (% by volume) |
| --- | --- |
| 1 | 95.8 |
| 5 | 98.2 |
| 8 | 97.6 |

The catalysts prepared according to the process of this invention show higher activities than that of the catalyst of Example 1, prepared according to the presently known art, in the process of 2,6-xylenol production.

In addition, the catalyst prepared as in Example 1 tends to lose its activity with time, as shown by means of long duration tests carried out in comparison to the catalyst of Example 3, whose activity remains substantially constant.

We claim:
1. Process for preparing catalysts on the basis of iron oxide and/or chromium oxide active in the reaction of alkylation of phenol or o-cresol with methanol to yield 2,6-xylenol in which:
  (a) hydrate oxides of iron and/or chromium are precipitated from aqueous solutions or soluble compounds of said elements;
  (b) the precipitate so obtained is separated and said separated precipitate is washed;
  (c) washed precipitate is granulated and the so obtained granules are dried;
  (d) said dried granules are calcined at high temperature; characterized in that an organic carboxylic acid salt of iron and/or chromium is added to and homogenized with the washed precipitate from stage (b), and/or the dried granules from stage (c) are impregnated with an aqueous solution of organic carboxylic acid salt of iron and/or chromium; the quantity of said salt of organic carbox- ylic acid being such as to supply a quantity of iron and/or chromium of from 5 to 60% relatively to the content of such elements in the catalyst finally obtained.

2. Process as claimed in claim 1, characterized in that in stage (a) hydrate oxides of iron and/or chromium are precipitated starting from aqueous solutions containing ferric nitrate, chromic nitrate and/or chromic acid, by means of the adding of aqueous ammonia, operating at temperatures of from room temperature (20°–25° C.) up to about 70° C.

3. Process as claimed in claim 2, characterized in that said aqueous solution additionally contains sodium silicate, antimony chloride and/or tin chloride.

4. Process as claimed in claim 1, characterized in that washed precipitate from stage (b) is homogenized with ammonium metavanadate.

5. Process as claimed in claim 1, characterized in that washed precipitate from stage (b) is homogenized with a salt of mono- or di-carboxylic organic acids, selected from the group consisting of oxalate, benzoate, formate, acetate and citrate of iron and/or chromium.

6. Process as claimed in claim 1, characterized in that drying of granules in stage (c) is carried out at temperatures of from about 95° to about 120° C.

7. Process as claimed in claim 1, characterized in that dried granules from stage (c) are impregnated with an aqueous solution of an organic mono- or di-carboxylic acid salt, selected from the group consisting of oxalate, benzoate, formate, acetate and citrate of iron and/or chromium.

8. Process as claimed in claim 7, characterized in that the granules are submitted to an impregnation step with an aqueous solution of sulphuric acid, before being impregnated with the aqueous solution of organic carboxylic acid salt of iron and/or chromium.

9. Process as claimed in claim 1, characterized in that the granules are impregnated, immediately before being calcined, with an aqueous solution of potassium carbonate, and the drying is then carried out at temperatures up to 180° C.

10. Process as claimed in claim 1, characterized in that stage (d) is carried out at 300°–500° C., for 3–10 hours, operating in an oxidizing, or reducing, or inert atmosphere.

11. Process as claimed in claim 1, characterized in that about 30% of iron and/or chromium is supplied as a salt of organic carboxylic acid.

* * * * *